US00PP22775P3

(12) United States Plant Patent
Korlipara

(10) Patent No.: US PP22,775 P3
(45) Date of Patent: Jun. 5, 2012

(54) *ECHINACEA* PLANT NAMED 'FIREBIRD'

(50) Latin Name: *Echinacea sp.*
Varietal Denomination: Firebird

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 295 days.

(21) Appl. No.: 12/798,837

(22) Filed: Apr. 12, 2010

(65) Prior Publication Data

US 2011/0252531 P1 Oct. 13, 2011

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP18,839 P2 * 5/2008 Korlipara ..... Plt./428
PP19,427 P2 * 11/2008 Korlipara ..... Plt./428

OTHER PUBLICATIONS

UPOV ROM GTITM Computer Database, GTI Jouve Retrieval Software 2011/10 Citation for 'Firebird'.*
Anonymous "*Echinacea* 'Firebird' PPAF" available at http://www.plantdelights.com accessed Sep. 30, 2011.*

* cited by examiner

*Primary Examiner* — Wendy C Haas
(74) *Attorney, Agent, or Firm* — Klarquist Sparkman, LLP

(57) ABSTRACT

A new and distinct *Echinacea* plant named 'Firebird' characterized by medium, red orange flowers in a shuttlecock shape, well-branched flower stalks, a low habit, and excellent vigor.

1 Drawing Sheet

Botanical denomination: *Echinacea* sp.
Variety designation: 'Firebird'.

The present invention relates to a new and distinct cultivar of *Echinacea* and given the cultivar name 'Firebird'. *Echinacea* is in the family Asteraceae. This new cultivar originated as a fourth generation seedling from a planned breeding program using the unpatented parents *Echinacea paradoxa* and *Echinacea purpurea* 'Ruby Giant' for the initial cross. The exact parents of this selection are unnamed proprietary, unreleased plants.

Compared to *Echinacea paradoxa,* an unpatented plant and the original pollen parent in the breeding line, the new variety is much shorter and has red orange rather than yellow inflorescences.

Compared to *Echinacea* 'Tiki Torch', U.S. Plant Pat. No. 18,839, the new variety is shorter and has red orange rather than bright orange flowers.

This new *Echinacea* cultivar is distinguished by:

1. medium, red orange flowers in a shuttlecock shape
2. well-branched flower stalks
3. short habit
4. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows nine-month-old plants of *Echinacea* 'Firebird' growing in the ground in the trial field in full sun in the field in late June in Canby, Oreg.

DETAILED PLANT DESCRIPTION

The following is a detailed description of the new *Echinacea* cultivar based on observations of 18-month old specimens growing in the ground in the field in full sun in the trial bed under typical outdoor conditions in Canby, Oreg. The plants had been moved from one trial field to another the fall before. Canby is in Zone 8 on the USDA Hardiness map Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, fifth edition.

Plant:

*Type.*—Herbaceous perennial.
*Hardiness.*—USDA Zones 4 to 9.
*Size.*—Grows to 41 cm wide and 60 cm tall to top of flowers.
*Form.*—Basal clump.
*Vigor.*—Excellent.
*Roots.*—Roots develop easily from cuttings from the crown.

Stem (flowering):

*Type.*—Ascending.
*Size.*—Branching up to 6 times to 39 cm tall (to the upper most leaves) and 7 mm wide at base.
*Number of stems from the crown.*—12.
*Internode length.*—2 cm to 6 cm.
*Surface texture.*—Strigose.

*Color.*—Yellow Green 145B mottled with Yellow Green 147B.

Leaf (basal):

*Type.*—Simple.

*Shape.*—Lanceolate.

*Arrangement.*—Basal.

*Blade size.*—Grows to 22 cm long and 8 cm wide.

*Margins.*—Entire, undulate.

*Apex.*—Acute.

*Base.*—Attenuate.

*Surface texture.*—Strigose on both sides.

*Venation.*—Pinnate.

*Color.*—Topside, Green 137A with the vein Yellow Green 147C and bottom side closest to Yellow Green 147B with the vein Yellow Green 147C.

*Petiole description.*—Grows to 21 cm long and 3 mm wide, strigose, Yellow Green 147C except base which is Greyed Purple 187A.

Leaf (stem):

*Type.*—Simple.

*Shape.*—Ovate to lanceolate.

*Arrangement.*—Alternate.

*Blade size.*—Grows to 12.5 cm long and 5 cm wide.

*Margins.*—Coarsely serrate to entire, undulate.

*Apex.*—Acute.

*Base.*—Attenuate, continuing down petiole, clasping.

*Surface texture.*—Strigose on both sides.

*Venation.*—Pinnate.

*Color.*—Topside, Yellow Green 146A with the vein Yellow Green 145C and bottom side closest to Yellow Green 147B with the vein Yellow Green 145C.

*Petiole description.*—Grows to 2.5 cm long and 6 mm wide, strigose, Yellow Green 146D except top side base Greyed Purple 187A.

Inflorescence:

*Type.*—Composite on terminal stalked heads.

*Number of flowering stems per plant in summer.*—16 from the crown, most branching.

*Flowering stem.*—Grows to 54 cm tall from the base of the plant to the terminal flower and can grow to 23 cm long from the top leaf to the base of a flower head; branched, 1 to 6 inflorescences per stem; diameter growing to 10 mm wide near the flower head; strigose, Yellow Green 145B mottled with Yellow Green 147B.

*Size.*—Grows to 9 cm wide and 8 cm deep as disc enlarges.

*Form.*—Ray florets held mostly perpendicular to the stem when first opening then dropping down at a 30 to 40 degree angle; mature disc is conic.

*Immature inflorescence.*—3.8 cm wide and 2.2 cm deep, ray florets held at a 40 degree angle and rolled up so only the back color shows, Greyed Purple 183A, disc Greyed Purple 187A.

*Ray florets.*—Without pistil or stamen, 17 to 30 in number, oblanceolate with the tip 3 toothed (each acute), entire margins, base attenuate, grows to 5 cm long and 11 mm wide, glabrous on both sides; topside a bicolor with the top half between Orange Red 31 A and Orange Red 35A and bottom half darkening to Red 45A (base Red Purple 59A), older flowers fade to Red Purple 61A at the base and blends into Greyed Orange 173C near the tip; bottom side Greyed Purple 184A fading to Greyed Red 182A.

*Disc florets.*—About 450 in number, with pistil and stamen, 11 mm long and 2 mm wide, each with one persistent, very stiff bract (14 mm long and Greyed Purple 187A on top ⅓ to Yellow Green 146A on middle ⅓, White 155A on bottom ⅓); corolla 5 mm long and 2 mm wide, 5 lobed, glabrous, Yellow Green 146B with Greyed Purple 187A on lobes and base, pistil 11 mm long, ovary 1.5 mm long, White 155A, style 6 mm long, Greyed Purple 187A with an extruding, 2-branched stigma spreading 2 mm wide, Greyed Purple 187; stamen 4 in number, 4.5 mm long, anthers 3 mm long and Greyed Purple N186A, filaments 1.5 mm long, Yellow Green 146C, pollen Yellow Orange 20A.

*Phyllaries.*—In 4 leafy series, area 32 mm wide and 8 mm deep, lobes lanceolate in shape, reflexed, grow to 7 mm long and 3 mm wide, margins strigose, tip acute, Yellow Green 147A.

*Receptacle.*—Grows to 12 mm wide and 25 mm deep, White 155B.

*Bloom period.*—July through October in Canby, Oreg.

*Fragrance.*—Light, floral.

*Lastingness.*—Each inflorescence lasts about two weeks in Canby, Oreg.

Seeds: Average number of 10 seeds/head, each 5 mm long and 2.5 mm wide, oval, Greyed Brown N199A.

*Fertility.*—Low.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea* 'Tomato Soup' (U.S. Plant Pat. No. 19,427), the new cultivar has more orange in the flower and fades to a bicolor rather than being red and fading to a dull red. The new cultivar has inflorescences that are shaped like a shuttlecock, rather than having petals perpendicular to the stem.

I claim:

1. A new and distinct *Echinacea* plant as herein illustrated and described.

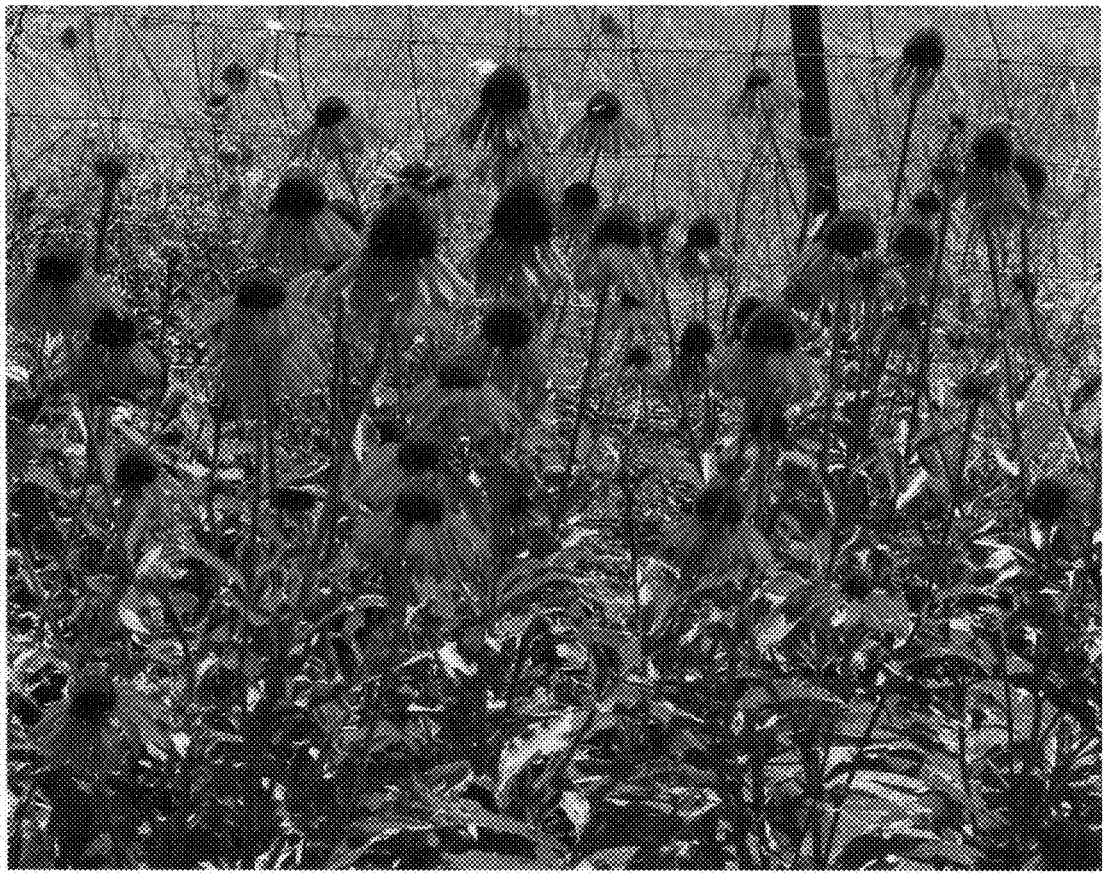

* * * * *